United States Patent [19]

Chappell et al.

[11] Patent Number: 5,260,053
[45] Date of Patent: * Nov. 9, 1993

[54] HERBAL DEODORANT

[75] Inventors: Katherine C. Chappell, Kennebunk, Me.; Pamela A. Scheeler, Portsmouth, N.H.; Gary Rittershaus, Kennebunkport, Me.

[73] Assignee: Tom's of Maine, Kennebunk, Me.

[*] Notice: The portion of the term of this patent subsequent to Oct. 26, 2010 has been disclaimed.

[21] Appl. No.: 866,199

[22] Filed: Apr. 9, 1992

Related U.S. Application Data

[63] Continuation-in-part of Ser. No. 814,569, Dec. 30, 1991.

[51] Int. Cl.$^5$ .................. A61K 7/32; A61K 35/82
[52] U.S. Cl. ............................. 424/65; 424/195.1
[58] Field of Search .................. 424/65, 401, 195.1

[56] References Cited

U.S. PATENT DOCUMENTS

| | | | |
|---|---|---|---|
| 4,002,775 | 1/1977 | Kabara | 426/532 |
| 4,014,995 | 3/1977 | Juliano | 424/71 |
| 4,883,651 | 11/1989 | Meyer | 424/47 |
| 4,921,694 | 5/1990 | Hoppe | 424/65 |
| 4,933,177 | 6/1990 | Grollier | 424/70 |
| 5,137,717 | 8/1992 | Wixforth | 424/78.07 |

FOREIGN PATENT DOCUMENTS

| | | |
|---|---|---|
| 1475226 | 6/1977 | United Kingdom . |
| 1590485 | 6/1981 | United Kingdom . |
| 1596791 | 8/1981 | United Kingdom . |
| 0077047A1 | 4/1983 | World Int. Prop. O. . |
| 0433911A1 | 6/1991 | World Int. Prop. O. . |

OTHER PUBLICATIONS

Webster's 9th New Collegiate Dictionary pp. 73, 290.

Primary Examiner—Thurman K. Page
Assistant Examiner—Sally Gardner
Attorney, Agent, or Firm—Fish & Richardson

[57] ABSTRACT

A deodorant composition for use in a liquid roll-on or stick deodorant has active antibacterial constituents consisting essentially of natural materials and is essentially free of petroleum derived constituents and alcohols. In a preferred embodiment of the composition for use as a liquid roll-on deodorant, the active antibacterial constituents consist essentially of about 1% to 6% (by weight) Lichen Extract and about 0.1% to 3% (by weight) Coriander Oil.

19 Claims, No Drawings

HERBAL DEODORANT

RELATED APPLICATIONS

This application is a continuation in part of U.S. Ser. No. 07/814,569, filed Dec. 30, 1991.

BACKGROUND OF THE INVENTION

The invention relates to a deodorant composition, e.g. for liquid roll-on or stick, employing only natural bactericides for personal use.

To be effective, a personal deodorant must, of course, reduce odor. It is known that odor in the axillary vault is caused by bacteria metabolizing the rich supply of proteins and lipids supplied by the apocrine sweat glands. The bacterial flora bound in the human axilla (or armpit) that are responsible for odor generation have been identified as gram positive lipophilic diphtheroids and micrococci. The diphtheroids produce the typical pungent axillary odor and the micrococci produce a sweaty isovaleric acid type odor. The moisture and minerals secreted by the eccrine sweat glands serve to enrich and replenish axilla flora.

In order for a deodorant to work properly, it must:

A) Cling tenaciously to the skin and resist washing away with eccrine sweat,

B) Sufficiently reduce populations of diphtheroids and micrococci and their subsequent metabolic end products, and C) Mask the presence of androgen steroids (produced by bacteria) which are detectable by the human nose at a concentration of a few parts per million.

The use of natural bactericides is known in the art. For example, Kabara U.S. Pat. No. 4,002,775 and Hoppe et al. U.S. Pat. No. 4,921,694 describe lauroyl monoesters of glycerin and synergistic mixtures having antibacterial activity. Also, EP Patent Publication No. 376761, German Patent Nos. 23 54 517, 23 51 927 and 23 51 864 and United Kingdom Patent Publication No. 1,475,226 describe the deodorizing effects of lichen acid, and especially usnic acid.

SUMMARY OF THE INVENTION

According to the invention, a deodorant composition has active antibacterial constituents consisting essentially of natural materials, and it is essentially free of petroleum derived constituents and alcohols.

According to one aspect of the invention, in preferred embodiments, the deodorant composition for a liquid roll-on deodorant consists essentially of the following ingredients, with the preferred ranges given by weight percent: (a) Glycerin, about 40% to 70%, preferably about 47 to 52%, and more preferably about 50%; (b) Chamomile Tea, about 10% to 50%, preferably about 18.8% to 22.8%, and more preferably about 20.8%; (c) Witch Hazel, about 5% to 25%, preferably about 16% to 20%, and more preferably about 18%; (d) Aloe Vera, about 5% to 20%, preferably about 8.0% to 12.0%, and more preferably about 10.0%; (e) Lichen Extract, about 1% to 6%, preferably about 1.8% to 2.2%, and more preferably about 2.0%; (f) Oat Flour, about 0.1% to 3%, preferably about 0.45% to 0.55%, and more preferably about 0.5%; (g) Coriander Oil, about 0.1% to 3%, preferably about 0.35% to 0.45%, and more preferably about 0.40%; and (h) Xanthan Gum, about 0.1% to 3.0%, preferably about 0.25% to 0.35%, and more preferably about 0.30%.

According to another aspect of the invention, in preferred embodiments, a deodorant composition for a stick deodorant consists essentially of the following ingredients, with the preferred ranges given by weight percent: (a) Glycerin, about 40% to 70%, preferably about 47% to 52%, and more preferably about 50%; (b) Chamomile Tea, about 20% to 60%, preferably about 32% to 36%, and more preferably about 34%; (c) Sodium Stearate, about 3% to 8%, preferably about 4.75% to 5.25%, and more preferably about 5.0%; (d) Witch Hazel, about 5% to 15%, preferably about 3.3% to 3.7%, and more preferably about 3.5%; (e) Aloe Vera, about 5% to 15%, preferably about 3.3% to 3.7%, and more preferably about 3.5%; (f) Lichen Extract, about 1% to 6%, preferably about 1.8% to 2.2%, and more preferably about 2.0%; (g) Oat Flour, about 0.1% to 3%, preferably about 1.2% to 1.3%, and more preferably about 1.25%; (h) Coriander Oil, about 0.1% to 3%, preferably about 0.38% to 0.42%, and more preferably about 0.40%; and (i) Glyceryl Monolaurate, about 0.1% to 0.6%, preferably about 0.38% to 0.42%, and more preferably about 0.40%.

According to another aspect of the invention, a deodorant composition has active antibacterial constituents consisting essentially of natural materials.

In preferred embodiments of this aspect of the invention, the deodorant composition for liquid roll-on and stick deodorants consists essentially of the following ingredients, with the preferred ranges given by weight percent: (a) Lichen Extract, about 1% to 6%, preferably about 1.8% to 2.2%, and more preferably about 2.0%; and (b) Coriander Oil, about 0.1% to 3%, preferably about 0.38 to 0.42%, and more preferably about 0.40%. In addition, the stick deodorant composition contains (c) Glyceryl Monolaurate, about 0.1% to 0.6%, preferably about 0.38 to 0.42%, and more preferably about 0.40%. The primary inactive constituent consists of glycerin. The composition is essentially free of petroleum derived constituents and alcohols.

These and other features and advantages of the invention will be seen from the following description of a presently preferred embodiment, and from the claims.

DESCRIPTION OF THE PRESENTLY PREFERRED EMBODIMENT(S)

The invention is a deodorant composition which contains natural antibacterial ingredients (e.g., lichen extract and coriander oil), and no petroleum derived ingredients or alcohol, to provide gentle protection with minimal cause for skin irritation. The composition is adaptable for use in a liquid roll-on deodorant, and for use in a stick deodorant.

Active Constituents

Deodorant compositions of the invention suitable for stick or liquid roll-on applications contain natural active constituents including coriander oil and lichen extract. These natural active constituents interact to accomplish odor prevention. The understanding of the role that each constituent plays based on in vivo, in vitro observations and theoretical considerations.

In the preferred formulation, coriander acts to reduce both micrococci and diphtheroids, and further serves to mask any lingering androsterone compounds. Coriander is composed mostly of oxygenated terpenoids that are weakly to moderately soluble in water. These terpenoids are, however, soluble in the phospholipid bi-layer of cell membranes and act to interfere with energy metabolism. It is understood that emulsifying terpenoids serve to enhance antimicrobial activity by increasing cell penetration potential. Coriander oil has a typical minimum inhibitory count of 0.1%, and the average zone of inhibition is 12 mm.

In the preferred composition, lichen extract also acts to reduce micrococci and diphtheroids. The active component in lichen extract is usnic acid. Usnic acid and its metal salt, sodium usnate, are potent, gram positive specific antibacterial compounds. The typical usnate content found in lichen extract is around 5.0%. A one percent level of lichen extract represents only 0.05% sodium usnate. Part for part, sodium usnate is as powerful as triclosan. Usnic acid is a dibenzofuran derivative and, in the metal salt form, it is readily soluble in water. It inhibits mitosis and cell respiration and easily permeates the cell wall of most gram positive bacteria. Sodium usnate has a typical minimum inhibitory count (MIC) of 0.002% and a minimal germicidal concentration (MGC) of 0.1%. The lichen extract would then have an MIC of 0.04 and an MGC of 2.0%. The zone of inhibition for lichen extract is about 40 mm.

In formulations suitable for application as a liquid roll-on deodorant, due to the pH of the composition and the acidic nature of the axillary vault, the application of the roll-on formulation distributes a dispersion of usnic acid on the skin's surface which then acts as a bactericide in the axillary vault. While the metal salt form of usnic acid is water soluble, the free form of usnic acid is not water soluble and will cling to the skin surface despite the presence of eccrine sweat.

In formulations suitable for applications as a stick deodorant, an emollient glycerol monolaurate is typically provided, in addition to coriander oil and lichen extract, due to the relatively high solubility of the metal salt form of usnic acid in water. The glycerol monolaurate serves to hold the usnic acid to the skin.

Glyceryl monolaurate is a tranester of glycerin and the lauric acid from coconut oil. It is a gram positive specific agent and has a minimum inhibitory concentration of 0.1%, with a zone of inhibition of about 15 mm. Glyceryl monolaurate acts as an emollient, oil emulsifier, and possesses the aforementioned antibacterial qualities. It helps to enhance the efficacy of coriander by making it more water soluble, and also serves to hold the lichen extract on the skin. The antibacterial action is only a consideration when the pH of the emollient reaches the range of from 6.0 to 7.0 in the axillary vault. The pH of the stick deodorant composition is in the range from 9.0 to 10.0 and activity would not be observed until normal skin pH is restored. The composition relies more specifically on its surfactant qualities and dry feel than antibacterial potential.

In formulations of the invention for use as a liquid roll-on deodorant, the proportions of active ingredients are typically as follows: lichen extract present in a range of about 1% to 6% by weight, and preferably in a range of about 1.8% to 2.2% by weight; and coriander oil present in a range of about 0.1% to 3% by weight, and preferably in a range of about 0.35% to 0.45% by weight.

In formulations of the invention for use as a stick deodorant, the proportions of active ingredients are typically as follows: lichen extract present in a range of about 1% to 6% by weight, and preferably in a range of about 1.8% to 2.2% by weight; coriander oil present in a range of about 0.1% to 3% by weight, and preferably in a range of about 0.38% to 0.42% by weight; and glyceryl monolaurate present in a range of about 0.1% to 0.6% by weight, and preferably in a range of about 0.38% to 0.42% by weight.

Inactive Constituents

A distinguishing factor of the invention composition from previous art is the incorporation of glycerin versus propylene glycol as the preferred humectant. While propylene glycol is antibacterial at a 10% solution level, glycerin in the composition of the invention is known to be bacteriostatic. With the potential for antibacterial enhancement aside, glycerine provides a moisturizing benefit with low skin irritation potential which is better than propylene glycol. In addition, the use of glycerin allows a break in the dependence upon petroleum derived ingredients.

The deodorant composition of the invention, suitable for both liquid roll-on deodorant and stick deodorant applications, typically includes the following inactive constituents:

Glycerin is present in the formulations for both application in a range of about 40.0 to 70.0 percent by weight, and preferably in a range of about 47.5 to 52.5 percent by weight.

Witch Hazel Distillate provides astringency without alcohol, which lessens the opportunity for skin irritation potential.

Aloe Vera provides soothing effects which minimize skin irritation potential.

Oat Flour contributes to the texture and application of the formulation, and it also acts as an absorbent to reduce the feel of wetness.

Chamomile Tea is another inactive ingredient.

In formulations suitable for applications as a stick deodorant, sodium stearate is also present as an inactive ingredient. Sodium stearate is used as the structurant of the deodorant stick, as it is one of the least allergy-causing of the sodium salts of fatty acids.

In formulations suitable for applications as a liquid roll-on deodorant, xanthan gum is included as a stabilizer.

In formulations of the invention for use as a liquid roll-on deodorant, the proportions of inactive ingredients (in addition to glycerin) are typically as follows: (b) chamomile tea present in a range of about 10% to 50% by weight, and preferably in a range of about 18.8% to 22.8% by weight; witch hazel present in a range of about 5% to 25% by weight, and preferably in a range of about 16% to 20% by weight; aloe vera present in a range of about 5% to 20% by weight, and preferably in a range of about 8.0% to 12.0% by weight; oat flour present in a range of about 0.1% to 3% by weight, and preferably in a range of about 0.45% to 0.55% by weight: and xanthan gum present in a range of about 0.1% to 3.0% by weight, and preferably in a range of about 0.25% to 0.35% by weight.

In formulations of the invention for use as a stick deodorant, the proportions of inactive ingredients (in addition to glycerin) are as follows: chamomile tea present in a range of about 20% to 60% by weight, and preferably in a range of about 32% to 36% by weight; sodium stearate present in a range of about 3% to 8% by weights, and preferably in a range of about 4.75% to 5.25% by weight; witch hazel present in a range of about 5% to 15% by weight, and preferably in a range of about 3.3% to 3.7% by weight; aloe vera present in a range of about 5% to 15% by weight, and preferably in a range of about 3.3% to 3.7% by weight; and oat flour present in a range of about 0.1% to 3% by weight, and preferably in a range of about 1.2% to 1.3% by weight.

The compositions, prepared in the form of a liquid roll-on deodorant or a stick deodorant, provide personal deodorant protection with reduced cause for skin irritation.

In a preferred embodiment for a liquid roll-on deodorant, the composition is as follows (by weight):

| | |
|---|---|
| Glycerin | 48.00% |
| Chamomile Tea | 20.80% |
| Witch Hazel | 18.00% |
| Aloe Vera | 10.00% |
| Lichen Extract | 2.00% |
| Oat Flour | 0.50% |
| Coriander Oil | 0.40% |
| Xanthan Gum | 0.30% |

The composition has a pH in the range of from 7.0 to 8.0.

In a preferred embodiment for a stick deodorant, the composition is as follows (by weight):

| | |
|---|---|
| Glycerin | 50.00% |
| Chamomile Tea | 33.95% |
| Sodium Stearate | 5.00% |
| Witch Hazel | 3.50% |
| Aloe Vera | 3.50% |
| Lichen Extract | 2.00% |
| Oat Flour | 1.25% |
| Coriander Oil | 0.40% |
| Glyceryl Monolaurate | 0.40% |

The composition has a pH in the range of from 9.0 to 10.0.

Other embodiments are within the following claims.

What is claimed is:

1. A deodorant composition with active antibacterial constituents consisting essentially of (by weight based upon total weight of the composition):
   a. about 1% to 6% Lichen Extract;
   b. about 0.1% to 3% Coriander Oil; and
   c. about 0.1% to 0.6% Glyceryl Monolaurate, said composition being essentially free of petroleum derived constituents and alcohols.

2. A liquid roll-on deodorant composition consisting essentially of (by weight) based upon total weight of the composition:
   a. about 40 to 70% Glycerin;
   b. about 10% to 50% Chamomile Tea;
   c. about 5% to 25% Witch Hazel;
   d. about 5% to 20% Aloe Vera;
   e. about 1% to 6% Lichen Extract;
   f. about 0.1% to 3% Oat Flour;
   g. about 0.1% to 3% Coriander Oil; and
   h. about 0.1% to 3% Xanthan Gum.

3. The liquid roll-on deodorant composition of claim 2 containing Glycerin in the range of about 47% to 52%, by weight based upon total weight of the composition.

4. The liquid roll-on deodorant composition of claim 3 containing about 50% by weight (based upon total weight of the composition) Glycerin.

5. The liquid roll-on deodorant composition of claim 2 containing chamomile Tea in the range of about 18.80% to 22.80%, by weight based upon total weight of the composition.

6. The liquid roll-on deodorant composition of claim 5 containing about 20.80% by weight (based upon total weight of the composition).

7. The liquid roll-on deodorant composition of claim 2 containing Witch Hazel in the range of about 16.0% to 20.0%, by weight based upon total weight of the composition.

8. The liquid roll-on deodorant composition of claim 7 containing about 18.00% by weight (based upon total weight of the composition) Witch Hazel.

9. The liquid roll-on deodorant composition of claim 2 containing Aloe Vera in the range of about 8.0% to 12.0%, by weight based upon total weight of the composition.

10. The liquid roll-on deodorant composition of claim 9 containing about 10% by weight (based upon total weight of the composition) Aloe Vera.

11. The liquid roll-on deodorant composition of claim 2 containing Lichen Extract in the range of about 1.8% to 2.2%, by weight based upon total weight of the composition.

12. The liquid roll-on deodorant composition of claim 11 containing about 2.0% by weight (based upon total weight of the composition) Lichen Extract.

13. The liquid roll-on deodorant composition of claim 2 containing Oat Flour in the range of about 0.45% to 0.55%, by weight based upon total weight of the composition.

14. The liquid roll-on deodorant composition of claim 13 containing about 0.5% by weight (based upon total weight of the composition) Oat Flour.

15. The liquid roll-on deodorant composition of claim 2 containing Coriander Oil in the range of about 0.35% to 0.45%, by weight based upon total weight of the composition.

16. The liquid roll-on deodorant composition of claim 15 containing about 0.40% by weight (based upon total weight of the composition) Coriander Oil.

17. The liquid roll-on deodorant composition of claim 2 containing Xanthan Gum in the range of about 0.25% to 0.35%, by weight (based upon total weight of the composition).

18. The liquid roll-on deodorant composition of claim 17 containing about 0.30% by weight (based upon total weight of the composition) Xanthan Gum.

19. A deodorant composition consisting essentially of (by weight based upon total weight of the composition):
   a. about 40 to 70% Glycerin;
   b. about 20% to 60% Chamomile Tea;
   c. about 3% to 8% Sodium Stearate;
   d. about 5% to 15% Witch Hazel;
   e. about 5% to 15% Aloe Vera;
   f. about 1% to 6% Lichen Extract;
   g. about 0.1% to 3% Oat Flour;
   h. about 0.1% to 3% Coriander Oil; and
   i. about 0.1% to 0.% Glyceryl Monolaurate.

* * * * *

UNITED STATES PATENT AND TRADEMARK OFFICE
CERTIFICATE OF CORRECTION

PATENT NO. : 5,260,053

DATED : November 9, 1993

INVENTOR(S) : Katherine C. Chappel et al.

It is certified that error appears in the above-identified patent and that said Letters Patent are hereby corrected as shown below:

Claim 6, column 6, line 10, after "composition", insert

--,Chamomile Tea--.

Signed and Sealed this

Twenty-first Day of June, 1994

Attest:

BRUCE LEHMAN

Attesting Officer Commissioner of Patents and Trademarks